United States Patent [19]

Turner

[11] 4,289,129
[45] Sep. 15, 1981

[54] INJECTION SITE APPARATUS

[76] Inventor: Roger S. Turner, 620 Carpenter La., Philadelphia, Pa. 19119

[21] Appl. No.: 90,499

[22] Filed: Nov. 1, 1979

[51] Int. Cl.³ .............................................. A61M 5/14
[52] U.S. Cl. .............................. 128/214 G; 128/214.2
[58] Field of Search .................. 128/214, 214 G, 347, 128/214.4, 214.2, 215

[56] References Cited

U.S. PATENT DOCUMENTS

| | | | |
|---|---|---|---|
| 3,313,299 | 4/1967 | Spademan | 128/214.4 |
| 3,739,778 | 6/1973 | Monestere, Jr. | 128/214 G |
| 3,861,388 | 1/1975 | Vaughn | 128/214 G |
| 4,043,333 | 8/1977 | Munsch | 128/214 G |
| 4,076,023 | 2/1978 | Martinez | 128/214 G |
| 4,121,585 | 10/1978 | Becker | 128/214 G |
| 4,122,944 | 9/1978 | Williams | 128/214 G |
| 4,184,489 | 1/1980 | Burd | 128/214 R |

Primary Examiner—Stephen C. Pellegrino
Attorney, Agent, or Firm—John B. Sowell

[57] ABSTRACT

An injection site apparatus is adapted to be attached to a continuous unbroken portion of a flexible tube of an intravenous delivery set. The apparatus is provided with a recessed channel for supporting and bending a portion of the flexible tube. The apparatus is provided with a piercable closure and a needle guide which are axially aligned with a portion of the recessed channel. The piercable closure and needle guide align a hypodermic needle in axial alignment with the center of said flexible tube to prevent interference therewith.

28 Claims, 8 Drawing Figures

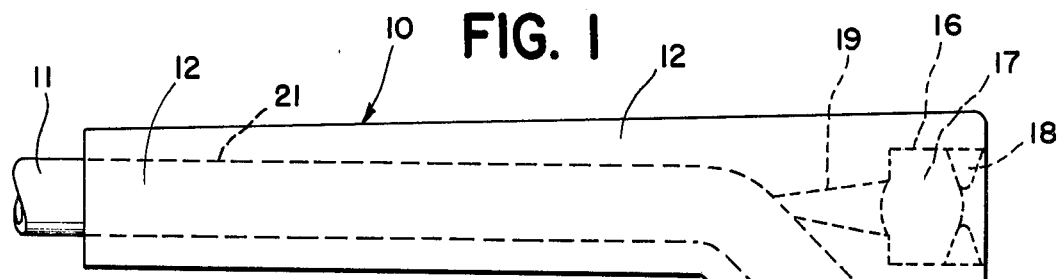
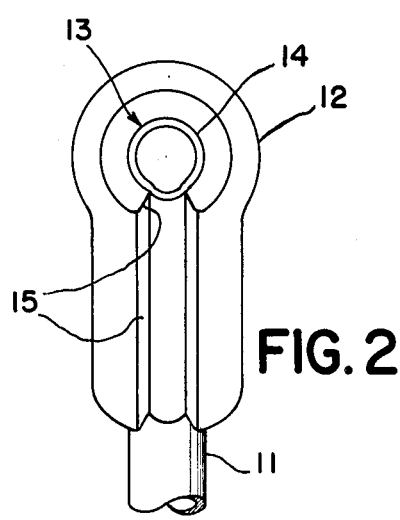
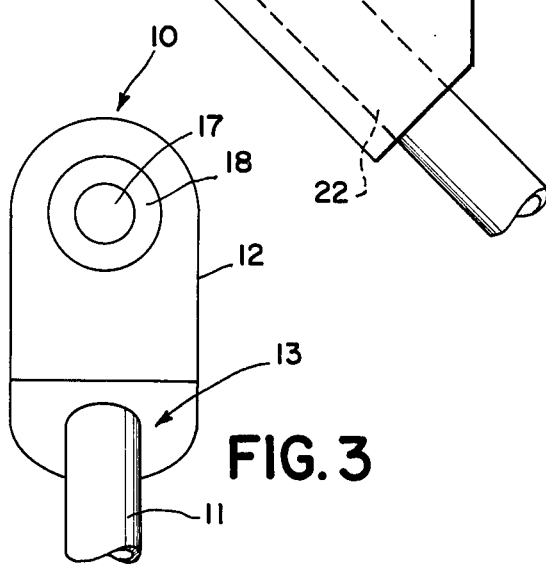
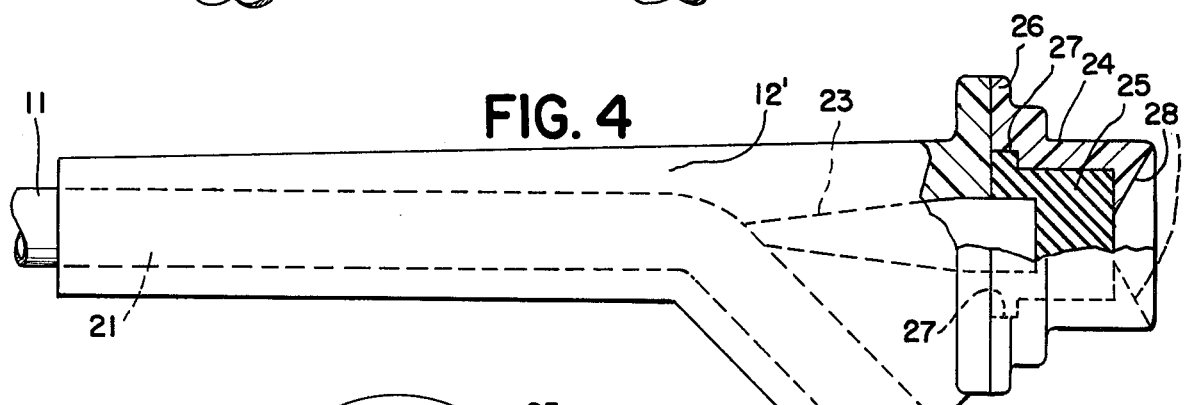
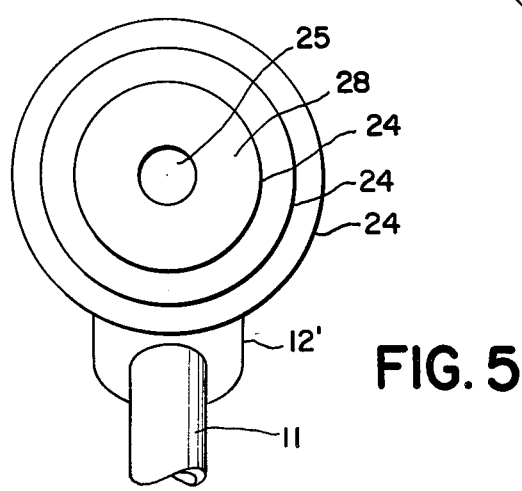

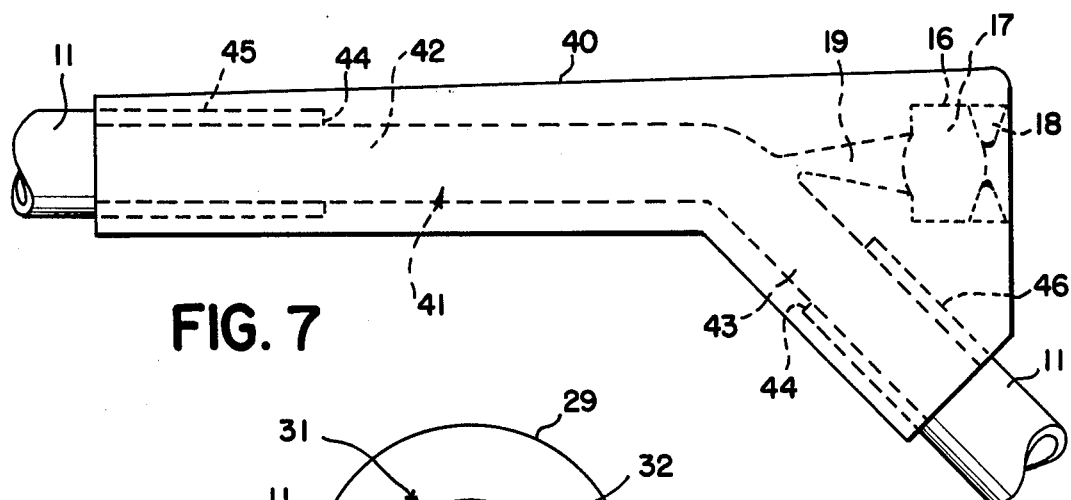
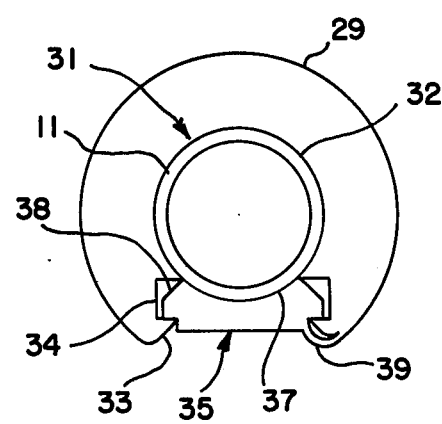
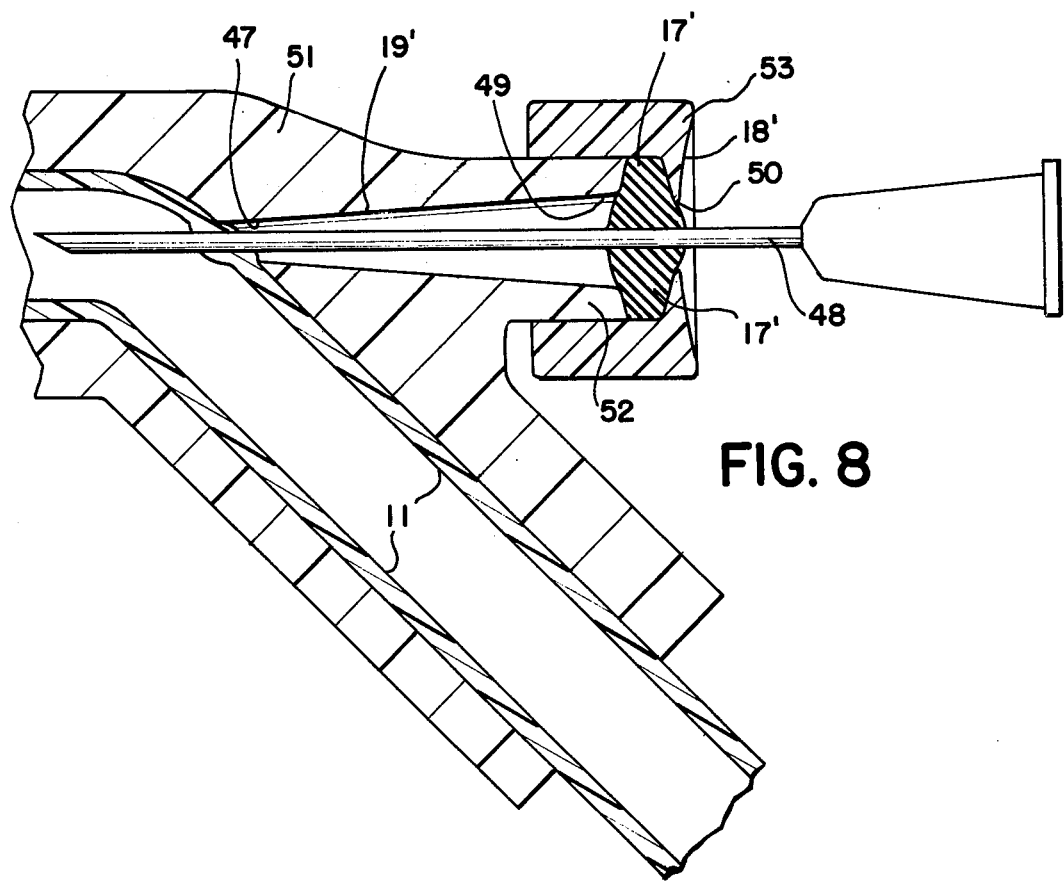

INJECTION SITE APPARATUS

BACKGROUND OF THE INVENTION

1. Field of the Invention

The present invention relates to apparatus employed to inject fluids into the flexible tube of an intravenous (I.V.) delivery set and more particularly relates to a novel injection site apparatus.

2. Description of the Prior Art

Several different types of injection site apparatus are presently commercially available. Prior art injection site apparatus require that the flexible tube of the intravenous set be cut or broken and that the injection site apparatus be inserted in series therewith. Connecting the severed ends or intermediate ends of the flexible tubes to the injection site apparatus presents several problems. When the flexible tube does not properly bond to the injection site housing leakage and/or contamination occurs. Prior art bonded connections have presented the possibility that an incomplete seal or weak seal will be made.

Most prior art injection site housings have spaces therein which entrap air. Further, the entrapped air can be administered to a patient when it passes out of the space in the injection site housing and into the flexible tube of the delivery set. The entrapped air in the prior art injection site apparatus could sometimes be removed with difficulty by inverting the housing, flushing and purging the air space in the injection site apparatus.

Some prior art injection site apparatus have no effective needle guides which permits the hypodermic needle to pierce the side of the housing or the flexible tube of the I.V. set or the connections between the housing and the flexible tube. It has been observed that such apparatus will permit the hypodermic needle to gouge into the housing so as to remove particles of the plastic housing which are flushed into the patient. The tip of the hypodermic needle can also become bent and unusable again. The hypodermic needle can become lodged into the side wall of the flexible tube so as to prevent flow of fluid. The hypodermic needle may be started into the side wall of a piercable closure in a manner which causes enough resistance to bend the hypodermic needle before it can enter into the fluid chamber of the injection site apparatus.

It would be desirable to eliminate the common problems of the prior art injection site apparatus in a simpler and cheaper structure.

SUMMARY OF THE INVENTION

It is an object of the present invention to provide a novel injection site apparatus.

It is another object of the present invention to provide an injection site apparatus which eliminates the possibility of air entrapped in the injection site housing from entering into the flexible tube of the I.V. delivery set.

It is another object of the present invention to provide a novel injection site apparatus which attaches to an unbroken portion of the flexible tube of an I.V. delivery set.

It is another object of the present invention to provide a simple an inexpensive injection site apparatus which enhances the ease of use.

It is another object of the present invention to provide an injection site apparatus which has a minimum number of surfaces to be sealed.

It is another object of the present invention to provide a novel needle guide for an injection site apparatus which eliminates the possibility of a hypodermic needle being inserted improperly into the apparatus.

Accordingly, there is provided an injection site apparatus having a recessed channel in the tube housing for receiving an unbroken section or portion of the flexible tube of an I.V. delivery set. The recessed channel supports and bends the flexible tube in the tube housing. A needle guide and a piercable closure in the housing are axially aligned with a portion of the flexible tube in the tube housing in a manner which directs the hypodermic needle through the side of the flexible tube and into the center or inside hollow area of the flexible tube.

BRIEF DESCRIPTION OF THE DRAWINGS

FIG. 1 is an enlarged side elevation view of a preferred embodiment injection site apparatus;

FIGS. 2 and 3 are end views of the injection site apparatus of FIG. 1;

FIG. 4 is an enlarged elevation view of a modified embodiment injection site apparatus;

FIG. 5 is an end view of the modified embodiment structure of FIG. 4;

FIG. 6 is an end view of yet another modified embodiment injection site apparatus;

FIG. 7 is an enlarged elevation of another modified embodiment injection site apparatus;

FIG. 8 is a modified partial section in elevation of the needle guide portion of the structure of FIG. 1.

DESCRIPTION OF THE PREFERRED EMBODIMENTS

Refer now to FIGS. 1 to 3 showing a preferred embodiment of the injection site apparatus 10. The flexible tube 11 of an I.V. delivery set is shown passing through tube housing 12. Tube housing 12 is provided with a recess channel 13 having a circular portion 14 and a converging tapered insert guide 15. The circular portion 14 embraces more than 180 degrees of the circumference of the flexible tube 11.

The flexible tube 11 and its tube housing 12 must provide a sterile environment. Accordingly, the injection site apparatus 10 may be sterilized after being placed on the flexible tube 11 employing prior art sterilizatation means or processes. Further, the flexible tube 11 may be snapped into the tube housing 12 with an antiseptic solvent type cement therebetween which provides self sterilization. Tube housing 12 is preferably made of a non-toxic grade of a semi-rigid plastic such as the polystyrenes, the polycarbonates and/or acrylics.

A piercable hypodermic closure receiver 16 is formed as a recess in the end of tube housing 12. A piercable closure 17 of the well known resilient type is mounted in the piercable closure receiver 16 and held in place therein by secondary needle guide 18 which also forms a sealing ring for compressing the piercable closure 17 in the receiver 16. Preferably, piercable closure 17 and receiver 16 are cylindrical in shape and the sealing ring 18 is formed as an annular ring.

Primary needle guide 19 is formed in the tube housing 12 intermediate the piercable closure receiver 16 and the recess channel 13. Recess channel 13 comprises an outlet portion 21 which is axially aligned with the primary needle guide 19 and the secondary needle guide 18. The inlet portion 22 of recess channel 13 is formed at an angle with outlet portion 21 so as to cause the flexible tube 11 to be bent and to expose a side wall surface to the small diameter end of primary needle guide 19. It will be understood that when a hypodermic needle is inserted through the secondary needle guide 18 it is guided through the center of the piercable closure 17 and into the large diameter end of the primary needle guide 19. Then it is aligned as it passes through the small diameter end of the primary needle guide 19 directly into alignment with the inside diameter of the flexible tube 11 in the outlet portion 21 of recess channel 13.

When the hypodermic needle is inserted through the side wall of flexible tube 11, there is no air introduced into the inside of the flexible tube 11 of the I.V. delivery set. When the hypodermic needle is removed from the flexible tube 11 of the I.V. delivery set, the flexible tube 11 closes at the puncture site so as to prevent leakage of fluid therefrom or air therein. The piercable closure 17 prevents any liquid that may seep out of the puncture hole in the flexible tube 11 from escaping from the tube housing 12 and also both seals and holds any air that was already in the primary needle guide 19 from being pulled into or pumped into the flexible tube 11.

Refer now to FIGS. 4 and 5 showing a modified embodiment structure of the preferred embodiment. Recess channel 13 of tube housing 12' is provided with an outlet portion 21 and an inlet portion 22. Also formed in tube housing 12' is a primary needle guide 23 which connects to the outlet portion 21. An extended cylindrical portion 24 of housing 12' forms a piercable hypodermic needle closure receiver for piercable closure 25. Portion 24 is provided with a sealing flange 26 and an aperture or recess 27 in the body or cylindrical portion 24. The secondary needle guide 28 is formed in the extended cylindrical portion 24 of housing 12'. It will be understood that the primary needle guide 23 is longer than the primary needle guide 19 and the secondary needle guide 28 is further removed from the outlet of the primary needle guide 23 so that a hypodermic needle is more accurately axially aligned with the center of the flexible tube 11. Further, the extended cylindrical portion 24 may be manufactured as a separate hat-shaped element and bonded onto a flange on tube housing 12'. The piercable closure 25 is shown as a molded hat-shaped part, but may be made in the form of a flat disk from flat sheet stock instead of making a molded part. The advantage of a flat disk shape piercable closure is that it is cheaper and the amount of resistance to a hypodermic needle may be more easily controlled.

Refer now to FIG. 6 showing an end view of another modified embodiment structure. Tube housing 29 has a recess channel 31 therein comprising a circular portion 32 and a converging tapered guide portion 33. Lock portion 34 of recess channel 31 is adapted to receive tube retainer 35 therein. Tube retainer 35 comprises a circular tube engaging portion 37 and a tube locking portion comprising tapered keys 38. Tube retainer 35 may be provided with a connector portion 39 which may be molded as a separate element.

The diameter of the circular portion of the tube housings 12 and 29 are made slightly smaller than the outside diameter of the flexible tubes 11 so that there is a slight compressive force applied by the tube housings. When tube retainer 35 is snapped into the lock portion 34, it is adapted to apply a slight compressive force similar to that being applied by the tube housings 12. By applying a continuous compressive force to the outside diameter of flexible tube 11, there is provided a pressure seal between the flexible tube 11 and the circular recess portion 32 of tube housing 29.

FIG. 7 shows another modified embodiment in which the preferred embodiment needle guides are integral with closed recess channel 41. Channel 41 is cylindrical in shape and comprises a cylindrical outlet portion 42 and a cylindrical inlet portion 43. The intermediate ends 44 of flexible tube 11 are adhesively bonded into cylindrical recess ends 45 and 46 of tube housing 40. Preferably the cylindrical portions 42 and 43 of the closed recess channel are approximately the same diameter as the inside diameter of the flexible tube 11. It will be understood that a hypodermic needle will be guided by the primary needle guide 19 and secondary needle guide 18 through the center of piercable closure 17 so as to enter the center of axially aligned outlet portion 42 of the recess channel 41 without engaging the side walls. The needle guide 18 is preferably provided with symmetrical tapers. Piercable closure receiver 16 is preferably tapered, thus, needle guide 18 may be machine assembled and ultrasonically welded in place without having to be oriented.

FIG. 8 shows a modified enlarged partial section in elevation of the novel needle guides 18 and 19. Primary needle guide 19' is preferably shaped as a converging cone having its reduced diameter outlet 47 terminating directly in engagement with the side wall of flexible tube 11. When the hypodermic needle 48 passes through the side wall of the flexible tube 11 it causes bulging of the tube against the hypodermic needle 48. In similar manner when the hypodermic needle 48 is inserted through the piercable closure 17', it causes bulging of the resilient piercable closure at the large diameter inlet 49 of the primary needle guide 19' and seals against the sides of needle 48. Secondary needle guide 18' is provided with a reduced diameter outlet 50 which has a larger diameter than the reduced diameter outlet 47 of the primary needle guide 19'. Preferably the large diameter inlet 49 of the primary needle guide 19' is larger than the reduced diameter outlet 50 of secondary needle guide 18'.

Housing 51 is shown having a cylindrical extension 52. A piercable closure receiver 53 is mounted on extension 52 and adapted to hold in compression piercable closure 17'. While the piercable closure 17' is shown with a bulge induced by the hypodermic needle 48, it will be understood that the compressive force of receiver 53 causes piercable closure 17' to extend outward into opening 50, thus, permitting piercable closure 17' to be easily wiped sterile prior to inserting hypodermic needle 48.

The injection sites shown in FIGS. 1, 4 and 8 are adapted to permit the novel needle guides 19, 23 and 19' and piercable closures 17, 25, and 17' to be leak tested prior to use. When an opening is provided in the flexible tube 11 at the needle guide opening 47, leak testing of flexible tube 11 also tests the seal of the piercable closure as well as the outside wall of flexible tube 11 against its housing. The opening in flexible tube 11 may be made prior to being inserted into its housing, at the time of insertion into its housing or by a needle inserted through the piercable closure after assembly of tube 11 into its housing and mounting of the piercable closure thereon.

It will be noted by examination of the enlarged FIG. 8 that the hypodermic needle 48 may be removed from flexible tube 11 and there is no requirement that the puncture in the side wall of flexible tube 11 be completely sealed. No air has been introduced into the inside diameter of flexible tube 11 by virtue of a hypodermic needle 48 being inserted there through, and the small amount of air which is entrapped in primary needle guide 19' cannot be pumped or forced out by the flow of the fluid inside of tube 11. The air in primary needle guide 19' is trapped in a manner which prevents it from entering tube 11 even though fluid from tube 11 may enter primary needle guide 19'.

I claim:

1. An injection site apparatus of the type adapted to be connected to a flexible tube of an intravenous delivery set, comprising:
    a tube housing,
    a recessed channel in said tube housing for receiving and retaining a continuous unbroken portion of said flexible tube,
    said recessed channel having a straight outlet portion and an adjoining inlet portion formed at an angle thereto for retaining said flexible tube at said angle in said recessed channel,
    a piercable hypodermic needle closure receiver on said tube housing,
    a primary needle guide connecting said piercable closure receiver with a portion of said recessed channel,
    a piercable closure mounted on said piercable closure receiver adapted to be punctured by a hypodermic needle, and
    a secondary needle guide provided on said piercable closure receiver adjacent said piercable closure,
    said hypodermic needle being insertable through said piercable closure and said needle guides to be guided into the center of said flexible tube.

2. An injection site apparatus as set forth in claim 1 wherein said needle guides are axially aligned with one of said recessed channel portions of said tube housing.

3. An injection site apparatus as set forth in claim 1 wherein said piercable closure receiver comprises a cavity in said tube housing.

4. An injection site apparatus as set forth in claim 3 wherein said secondary needle guide further provides an annular sealing ring fitted in said cavity for retaining said piercable closure in the bottom of said cavity.

5. An injection site apparatus as set forth in claim 4 wherein said sealing ring in said cavity applies compressive force on said piercable closure.

6. An injection site apparatus as set forth in claim 4 wherein said sealing ring is provided with a tapered annular portion adapted to guide a hypodermic needle into the center of said flexible tube.

7. An injection site apparatus as set forth in claim 6 wherein said sealing ring is provided with symmetrical tapered annular portions, one adapted to guide a hypodermic needle into said needle guide and the other adapted to compress said piercable closure into the bottom of said cavity.

8. An injection site apparatus as set forth in claim 4 wherein said annular sealing ring is provided with a central aperture axially aligned with said needle guide for directing said hypodermic needle into the center of said flexible tube.

9. An injection site apparatus as set forth in claim 3 wherein said piercable closure comprises a cylindrical shaped disc of resilient material.

10. An injection site apparatus as set forth in claim 3 wherein said cavity is provided with tapered sidewalls.

11. An injection site apparatus as set forth in claim 1 wherein said recessed channel comprises sidewall portions having a circular shaped cross-section for receiving said flexible tube therein.

12. An injection site apparatus as set forth in claim 11 which further includes a tube retainer forming a closure for said recessed channel.

13. An injection site apparatus as set forth in claim 12 wherein said tube retainer is provided with a tube engaging portion and a locking portion.

14. An injection site apparatus as set forth in claim 13 wherein said channel locking portion comprises a tapered key and said recessed channel further comprises a converging tapered insert guide portion.

15. An injection site apparatus as set forth in claim 14 wherein said recessed channel further includes a lock portion adapted to receive said tapered key of said tube retainer.

16. An injection site apparatus as set forth in claim 14 wherein said piercable closure further comprises a sealing flange.

17. An injection site apparatus as set forth in claim 11 wherein the diameter of said circular shaped cross-section is smaller than the diameter of said flexible tube.

18. An injection site apparatus as set forth in claim 1 wherein said recessed channel has a restricted opening for receiving and retaining said flexible tube, said restricted opening having a width less than the diameter of said flexible tube.

19. An injection site apparatus as set forth in claim 18 wherein said channel opening is provided with a converging tapered insert guide at the opening.

20. An injection site apparatus as set forth in claim 1 wherein said piercable closure receiver comprises a cylindrical extension of said tube-housing.

21. An injection site apparatus as set forth in claim 20 wherein said piercable closure receiver is provided with a cylindrical recess adapted to receive a cylindrical shaped piercable closure.

22. An injection site apparatus as set forth in claim 20 wherein said needle guide extends through said piercable closure receiver and terminates in a wide conical opening.

23. An injection site apparatus of the type adapted to be connected to the intermediate ends of a flexible tube of an I.V. delivery set, comprising:
    a tube housing,
    a hollow channel in said tube housing adapted to receive said intermediate ends of said flexible tube,
    said hollow channel having a cylindrical outlet portion and a connecting cylindrical inlet portion formed at an angle thereto,
    a piercable hypodermic needle closure receiver on said tube housing axially aligned with said outlet portion of said hollow channel,
    a primary needle guide formed in said tube housing between said piercable hypodermic needle closure receiver and said outlet portion of said hollow channel,
    said primary needle guide having a converging shape terminating at its small end in an outlet which is smaller than the inside diameter of said flexible tube, a piercable closure mounted in said piercable hypodermic needle closure receiver, and a secondary needle guide having an inlet axially aligned with said primary needle guide, said secondary needle guide forming means for aligning a hypodermic needle with the inside diameter of said flexible tube.

24. An injection site apparatus as set forth in claim 23 wherein said secondary needle guide comprises a converging shape terminating at its small end in an outlet which is larger than the inlet in said primary needle guide.

25. An injection site apparatus as set forth in claim 23 wherein said outlet in said secondary needle guide is larger than the outlet end of said primary needle guide.

26. An injection site apparatus as set forth in claim 23 wherein said cylindrical inlet portion and said cylindrical outlet portion of said hollow channel further comprise cylinders having substantially the same inside diameter as the inside diameter of said flexible tube.

27. An injection site apparatus as set forth in claim 23 wherein said cylindrical inlet portion and said cylindrical outlet portion of said hollow channel are provided with recessed ends having substantially the same diameter as the outside diameter of said flexible tube.

28. An injection site of the type adapted to guide a hypodermic needle into the interior of a flexible tube of an I.V. delivery set, comprising:

a tube housing, a hollow channel in said tube housing adapted to receive the intermediate ends of said flexible tube, said hollow channel having a cylindrical outlet portion and a connecting cylindrical inlet portion formed at an angle thereto, a primary needle guide formed in said tube housing in axial alignment with said cylindrical outlet portion, said primary needle guide comprising a narrow tapered conical shape terminating at its small end in an outlet connected to said cylindrical outlet portion, a piercable closure mounted in said tube housing adjacent the large end of said primary needle guide, and a secondary needle guide mounted in said tube housing in axial alignment with said piercable closure, said primary needle guide and said cylindrical outlet portion of said hollow channel, whereby a hypodermic needle inserted through said needle guides and said piercable closure is guided into the center of said hollow channel.

* * * * *